United States Patent [19]
Ichikawa

[11] Patent Number: 5,694,208
[45] Date of Patent: Dec. 2, 1997

[54] SENSOR FOR DETECTING FINE PARTICLES SUCH AS SMOKE OR DUST CONTAINED IN THE AIR

[75] Inventor: Nobuyuki Ichikawa, Tokyo, Japan

[73] Assignee: Nohmi Bosai Ltd., Tokyo, Japan

[21] Appl. No.: 617,627

[22] Filed: Mar. 19, 1996

[30] Foreign Application Priority Data

Mar. 24, 1995 [JP] Japan .................. 7-066465
Mar. 24, 1995 [JP] Japan .................. 7-066466

[51] Int. Cl.$^6$ .................................. G01N 21/00
[52] U.S. Cl. .................. 356/73; 356/438; 356/439; 356/338
[58] Field of Search .................. 356/73, 436–439, 356/43, 51, 338, 205; 340/505, 510, 511, 514, 518, 501, 506, 587, 588, 628, 630; 250/238, 214 R, 214 C, 575, 564, 565, 574, 573

[56] References Cited

U.S. PATENT DOCUMENTS

| | | | |
|---|---|---|---|
| 3,881,112 | 4/1975 | Roberts | 250/565 |
| 3,980,997 | 9/1976 | Berns et al. | 340/237 |
| 3,982,130 | 9/1976 | Trumble | 250/373 |
| 4,338,577 | 7/1982 | Sato et al. | 372/36 |
| 4,420,746 | 12/1983 | Malinowski | 340/630 |
| 4,481,506 | 11/1984 | Honma | 340/630 |
| 4,695,714 | 9/1987 | Kimizuka et al. | 250/205 |
| 4,700,057 | 10/1987 | Sakai | 250/205 |
| 4,819,241 | 4/1989 | Nagano | 372/38 |
| 4,823,015 | 4/1989 | Galvin et al. | 250/564 |
| 5,008,559 | 4/1991 | Beyersdorf | 250/575 |
| 5,045,683 | 9/1991 | Kanda | 250/205 |
| 5,477,218 | 12/1995 | Mammoto et al. | 340/630 |
| 5,497,009 | 3/1996 | Torikoshi et al. | 250/574 |
| 5,521,375 | 5/1996 | Jang | 250/238 |
| 5,552,763 | 9/1996 | Kirby | 340/506 |

FOREIGN PATENT DOCUMENTS

| | | |
|---|---|---|
| 0 596 500 | 5/1994 | European Pat. Off. . |
| 0 618 555 | 10/1994 | European Pat. Off. . |
| 21 14 107 | 2/1981 | Germany . |
| 2 259 761 | 3/1993 | United Kingdom . |
| 2 274 333 | 7/1994 | United Kingdom . |

*Primary Examiner*—Frank G. Font
*Assistant Examiner*—Michael P. Stafira
*Attorney, Agent, or Firm*—Wenderoth, Lind & Ponack

[57] ABSTRACT

An LD light-emitting circuit 2 comprises an analog multiplexer MP having a plurality of switches, and resistors R7, R8, R9 and R10 connected to these switches. When the temperature is not higher than a normal temperature, the resistor R7 is connected so that the amount of light emitted from the LD 1 is maintained constant. As the temperature rises, however, the resistor R8, R9 or R10 having increasing resistance is connected in response to a signal from a control circuit, in order to decrease the driving current that flows into the LD 1. This enables the LD 1 to suppress its own heating and to lengthen its life.

16 Claims, 7 Drawing Sheets

SENSOR FOR DETECTING FINE PARTICLES SUCH AS SMOKE OR DUST CONTAINED IN THE AIR

BACKGROUND OF THE INVENTION

1. Field of the Invention

The present invention relates to a photoelectric sensor for detecting fine particles such as smoke produced by a fire or dust contained in air and, particularly, to a sensor for detecting fine particles which features an extended life for the laser diode (LD) used as a light source thereof. The invention further relates to a sensor for detecting fine particles which features a broad dynamic range and which, when the alarm level is set to a low sensitivity, decreases the electric current for driving the light source to decrease the amount of light that is emitted, thereby decreasing the consumption of electric power and prolonging the life of the light source.

2. Description of the Prior Art

In general, in sensors for detecting fine particles such as highly sensitive smoke sensors or dust monitors, light is emitted from a light source to a detection area, and the light scattered by fine particles present in the detection area is detected, thereby detecting fine particles. As the light source, an LED (light-emitting diode), an LD (laser diode), a xenon lamp, or the like is usually used.

In a sensor for detecting fine particles using, for example, an LD as a light source for sensitive particle detection, an optical system with a high S/N ratio must generally be used to obtain a high resolution (i.e., a steep slope for fine particle concentration to sensor output characteristics). To realize highly sensitive detection, the LD must emit large amounts of light to increase the amount of scattered light or a large gain amplifier must be used to increase sensor output (voltage).

However, the alarm level, i.e., the setpoint value for an increase in the amount of fine particles in the case of, for example, the generation of a fire, etc. usually changes depending upon where the sensor is installed, and therefore is determined depending upon environmental conditions. That is, the alarm level is set to be highly sensitive in very clean places but is set to a sensitivity lower than the above-mentioned sensitivity (high sensitivity) in places where fine particles are present to some extent at all times.

Generally, when sensitivity is changed within the sensor, the value obtained by amplifying scattered light received is compared with the alarm level whereby an alarm decision is carried out, and the alarm level is then changed to change the sensitivity. That is, sensitivity is changed by changing the reference level of a comparator. Even when sensitivity is changed by a control unit such as a fire control panel connected to the sensor for detecting fine particles, the alarm decision is carried out by the comparator upon receiving the sensor output.

Generally, the amount of light emitted from the LD changes depending upon the temperature; i.e., the amount of light emitted decreases with an increase in temperature despite the fact that the same driving current is supplied. Therefore, in order to emit the same amount of light as emitted when the temperature is low, the driving current must be increased. However, running a driving current equal to or larger than a predetermined value results in the destruction of the LD. Even if the predetermined value is not reached, a large driving current gives rise to the generation of heat and like general semiconductor elements, use of the device under high-temperature conditions adversely affects the life thereof to a considerable degree. Furthermore, as described above, the conventional sensor for detecting fine particles has been designed to detect fine particles while maintaining a high sensitivity. Therefore, even when the sensitivity level is changed to a low level, the LD still emits light in large amounts consuming the driving current in large amounts, shortening its life.

SUMMARY OF THE INVENTION

The present invention has been accomplished in order to solve the above-mentioned problems, and its object is to provide a sensor for detecting fine particles wherein the life of the LD as the light source is increased.

Another object of the present invention is to provide a sensor for detecting fine particles which, when sensitivity is set at a low level, decreases the driving current supplied to the light source to decrease the amount of light emitted without changing the alarm level, thereby decreasing the consumption of electric power and increasing the life of the light source.

A further object of the present invention is to broaden the dynamic range of the sensor.

According to the present invention, there is provided a sensor for detecting fine particles comprising a light source, a light-emitting circuits electrically connected to the light source to emit light therefrom, light-receiver producing a sensor output upon detecting light emitted from the light source and scattered by fine particles, and a controller electrically connected to the light-emitting circuit in order to control the quantity to-be-controlled of the light source.

According to the present invention, there is further provided a sensor for detecting fine particle further comprising a temperature-measuring elements provided near the light source for measuring its temperature.

In the sensor for detecting fine particles of the present invention, light emitted from the light source is scattered by fine particles such as smoke produced by a fire or dust contained in air, and the light-receiver receives the scattered light thereby detecting the presence of fine particles. Based upon the temperature measured by the temperature-measuring element installed near the light source, the controller controls the quantity to-be-controlled of the light source.

DETAILED DESCRIPTION OF THE PREFERRED EMBODIMENTS

Embodiment 1

An embodiment of the present invention will now be described in detail with reference to the accompanying drawings.

Figure 1:
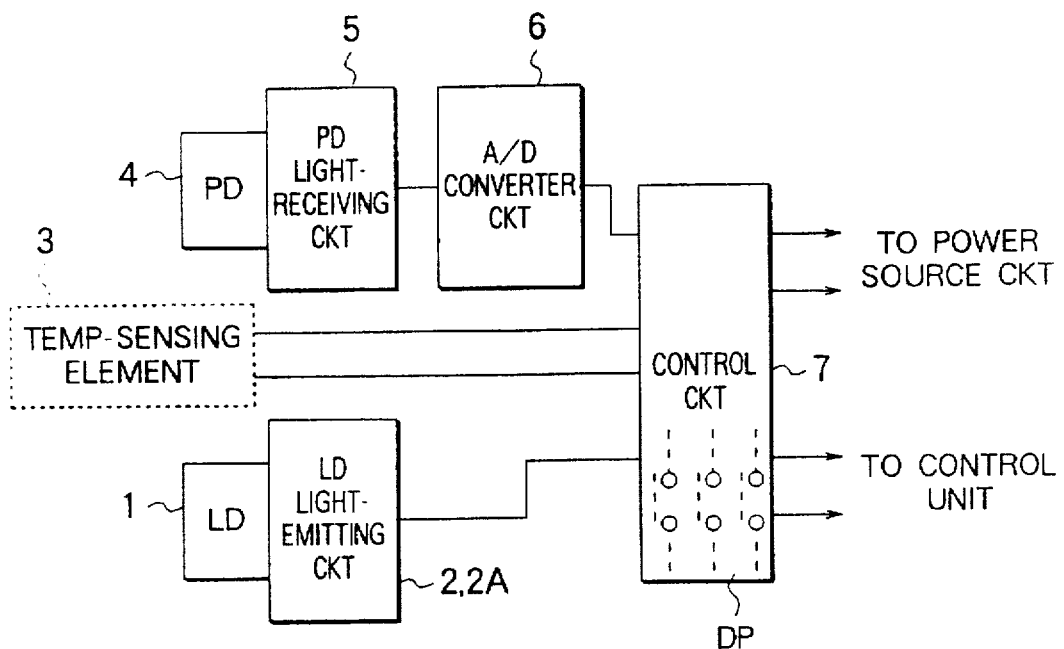
FIG. 1 is a block diagram of a sensor for detecting fine particles according to an embodiment of the present invention.

FIG. 1 is a block diagram illustrating an embodiment of a sensor for detecting fine particles according to the present invention, wherein reference numeral 1 denotes a light source such as an LD (laser diode), 2 denotes a light-emitting means such as an LD light-emitting circuit which is electrically connected to the LD 1 causing the LD 1 to emit light and maintaining a constant light emission, 3 denotes a temperature-measuring means or a temperature-sensing element such as a thermistor that is provided near the LD 1 to measure its temperature, 4 denotes a photo diode (PD) for producing a sensor output, 5 denotes a PD light-receiving circuit which is electrically connected to the PD 4 for producing the sensor output and which produces a sensor output upon detecting light emitted from the LD 1 and scattered by fine particles such as smoke produced by a fire or dust contained in air, and reference numeral 6 denotes an A/D converter circuit which is electrically connected to the PD light-receiving circuit 5 for analog/digital (A/D) conversion of the sensor output. The PD 4 for producing the sensor output, PD light-receiving circuit 5 and A/D converter circuit 6 constitute a light-receiving means. Reference numeral 7 denotes a control circuit such as a one-chip microcomputer which serves as a control means. This control circuit 7 includes a microprocessor, a ROM and RAMs 1 to 4 (not shown), is electrically connected to the above-mentioned LD light-emitting circuit 2, to temperature-sensing element 3 and to the light-receiving means, particularly, to the A/D converter circuit 6, and is further connected to a power source circuit (not shown) and to a control unit such as fire control panel (not shown). The control circuit 7 controls the LD 1 and LD light-emitting circuit 2 as will be described later in detail.

Figure 2:
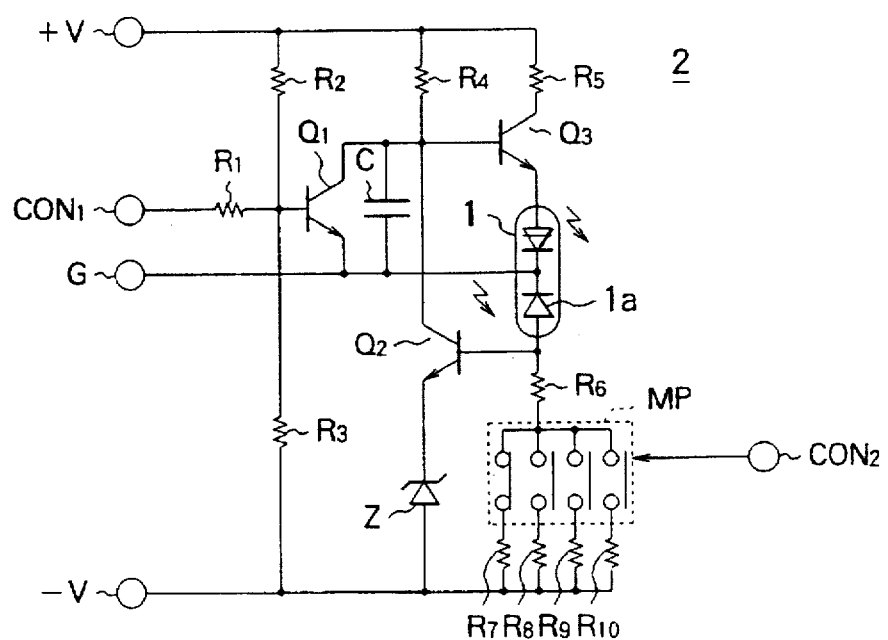
FIG. 2 is a diagram illustrating the LD light-emitting circuit shown in the block diagram of FIG. 1.

FIG. 2 is a circuit diagram concretely illustrating the LD 1 and the LD light-emitting circuit 2 shown in FIG. 1. The LD 1 includes a photo diode (PD) 1a for monitoring the amount of emitted light. A current that varies in proportion to the amount of light emitted by LD 1 flows into the PD 1a that monitors the amount of emitted light.

In FIG. 2, terminals CON1 and CON2 are connected to the control circuit 7, terminals +V and −V are connected to the +terminal and to the −terminal of the power source (not shown), respectively, and a terminal G is grounded. An NPN-type transistor Q1 is connected at its base to the terminal CON1 via an input resistor R1, to the terminal +V via a voltage-dividing resistor R2 and to the terminal −V via a voltage-dividing resistor R3. Furthermore, the emitter of the transistor Q1 is connected to the terminal G, and the capacitor C is connected between the collector and the emitter thereof. An NPN-type transistor Q2 is connected at its collector to the collector of the transistor Q1, to the terminal +V via a bias resistor R4, and at its emitter to the terminal −V via a Zener diode Z. An NPN transistor Q3 is connected at its base to the collectors of the transistors Q1 and Q2, at its collector to the terminal +V via a resistor R5, and at its emitter to the terminal G via an LD portion of the LD 1.

Furthermore, the PD 1a contained in the LD 1 for monitoring the amount of emitted light is connected between the terminal G and the base of the transistor Q2. The point at which the PD 1a for monitoring the amount of emitted light is connected to the base of the transistor Q2, is connected to the terminal −V via a resistor R6, an analog multiplexer MP having a plurality of switches, for example, four switches as shown in FIG. 2, resistors R7, R8, R9 or R10 corresponding to a closed switch (these resistors have resistances R7<R8<R9<R10). The switch in the analog multiplexer MP is selected and closed by a signal fed to the terminal CON2 from the control circuit 7 depending upon the temperature of the LD 1 measured by the temperature-sensing element 3, and whereby a corresponding resistor is connected. Here, the analog multiplexer MP and the resistors R7 to R10 constitute a driving current-decreasing means.

Figure 3:
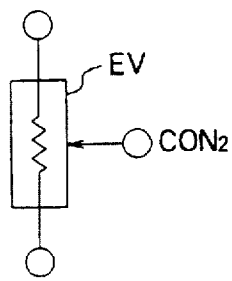
FIG. 3 is a diagram of an electron volume device used instead of the analog multiplexer and a plurality of resistors of FIG. 2.

The driving current can be set more finely if use is made of an electron volume device EV shown in FIG. 3 in place of the analog multiplexer MP and the resistors R7 to R10.

The LD 1 and the LD light-emitting circuit 2 are constituted as described above. When a signal of high potential supplied to the terminal CON1 from the control circuit 7 is further supplied to the base, the transistor Q1 is turned "ON" and its collector becomes a low potential nearly equal to ground potential. This low potential is applied to the base, and so the transistor Q3 remains turned "OFF". Therefore, no driving current flows into the LD 1 which then does not emit any light.

However, when a signal of low potential is supplied to the terminal CON1 from the control circuit 7, this signal is further supplied to the base so that the transistor Q1 is turned "OFF" and the collector assumes a high potential divided by a voltage drop across the resistor R4, the collector-emitter voltage Vce of the transistor Q2 and a voltage of the Zener diode Z. This high potential is applied to the base of the transistor Q3. In this case, the transistor Q3 has been set to operate not in the switching state but in the activated region. Therefore, the transistor Q3 assumes an active state in which the Vce is not saturated, the driving current determined by Vce and resistor R5 is allowed to flow, and the LD 1 emits light with this driving current, i.e., with the quantity to-be-controlled of the LD 1. Thus, by alternately supplying a signal of high potential and a signal of low potential to the terminal CON1 from the control circuit 7, the LD1 intermittently emits light.

As the LD 1 emits light, the PD 1f for monitoring the amount of emitted light generates a current in proportion to the amount of emitted light. This current flows into the terminal −V through the resistor R6 and, for example, the extreme left switch (for normal temperature or lower temperatures) in the analog multiplexer MP that is currently selected by a signal from the control circuit 7, and the resistor R7 connected to this switch, to thereby produce the base electric potential of the transistor Q2. When the LD 1 emits light in large amounts, the PD 1a for monitoring the amount of emitted light produces a large current, thereby generating a high base potential for the transistor Q2. Therefore, Vce of the transistor Q2 and the collector potential of the transistor Q2 decrease, i.e., the base potential of the transistor Q3 decreases, the Vce of the transistor Q3 increases, a decreased driving current flows into the LD 1, and light is emitted in small amounts. Conversely, as the amount of emitted light decreases as described above, the PD 1a for monitoring the amount of emitted light produces a small current, thereby generating a low base potential for the transistor Q2, whereby the Vce of the transistor Q2 and the base potential of the transistor Q3 increase, an increased driving current flows into the LD 1 and light is emitted in large amounts. As described above, the LD light-emitting circuit 2 operates to keep constant the amount of light emitted by the LD 1.

The LD monitoring currents for the amount of light emitted have been individually predetermined for their LDs. Therefore, the PD current for monitoring the amount of emitted light can be specified for the amount of emitted light required, whereby the resistances of the resistors R6 and R7 are determined based upon the above current.

To describe the above in further detail, if the temperature of the LD 1 as measured by the temperature-sensing element 3 is lower than a normal temperature, i.e., if the driving current set for the LD 1 is smaller than a maximum current specified at each temperature or is smaller than a value obtained by multiplying the set driving current by a safety factor determined by a user, the above-mentioned resistor R7 is selected, and the quantity to-be-controlled, i.e., the driving current of the LD 1 is controlled by a feedback operation, so that the LD 1 emits light in a constant amount.

Figure 4:
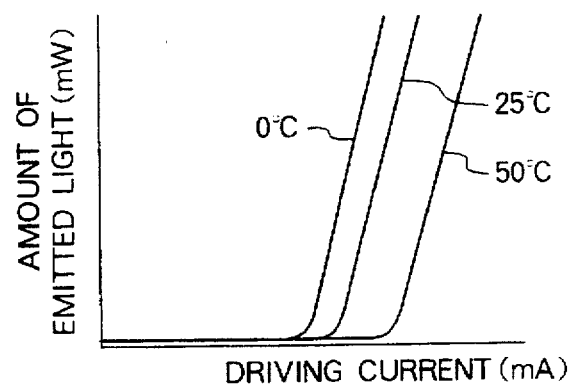
FIG. 4 is a graph illustrating characteristics of the LD.

FIG. 4 is a graph illustrating the temperature characteristics of the LD. As will be obvious from this graph, when the same driving current is supplied to the LD 1, the amount of light emitted by the LD 1 decreases with an increase in temperature. Therefore, in order to maintain a constant light emission, it inevitably becomes necessary to increase the driving current. That is, due to the action of the LD light-emitting circuit 2 to maintain a constant amount of emitted light at all times, the current that flows into the LD 1 increases, accelerating its self heating, which has an adverse effect on its own life. According to the present invention, therefore, when the temperature of the LD 1 as measured by the temperature-sensing element 3 is not lower than normal but instead is a temperature which is so high as to be a problem for the light source, the control circuit 7 selects and closes the switch to which is connected, for example, the resistor R8 having a resistance larger than the resistor R7 instead of the switch to which the resistor R7 is connected in the analog multiplexer MP (the switch to which the resistor R7 is connected is opened, as a matter of course). Resistance thus increases. Therefore, when the same current as the one that flowed into the resistor R7 flows into the resistor R8, the voltage drop across the latter increases and, hence, the base potential of the transistor Q2 increases, whereby as a result of the above-mentioned feedback operation, the quantity to be controlled, i.e., the driving current of the LD 1, decreases, the amount of light emitted varies, the rise in temperature of the LD 1 due to self heating is suppressed, and the life of the LD 1 is increased.

As the temperature of the LD 1 further increases, the resistor R9 is selected and connected instead of the resistor R8, or the resistor R10 is selected and connected instead of the resistor R9, whereby the driving current gradually decreases and the temperature rise of the LD 1 is suppressed.

Figure 5:
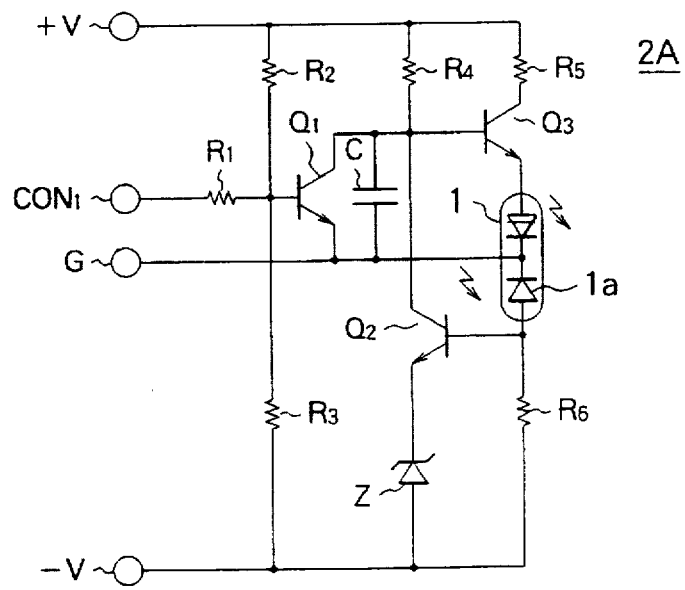
FIG. 5 is a diagram illustrating another LD light-emitting circuit.

FIG. 5 is a diagram illustrating another LD light-emitting circuit used for the sensor for detecting fine particles shown in FIG. 1. The difference between this LD light-emitting circuit and that of FIG. 2 is that this LD light-emitting circuit does not have an analog multiplexer MP, input terminal CON2 thereof or resistors R7~R10, and further, the other end of the resistor R6 is directly connected to the terminal –V.

Figure 6:
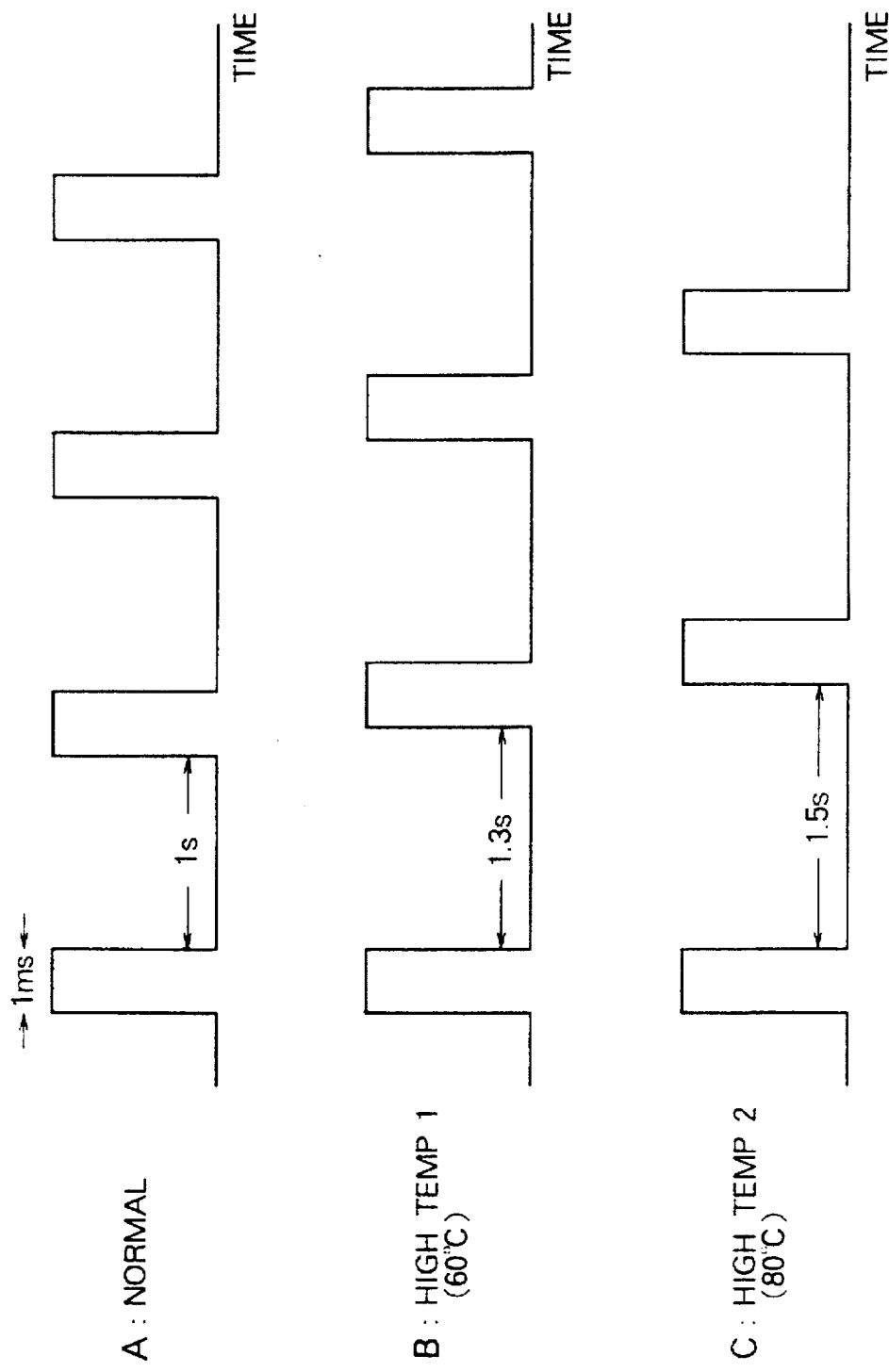
FIG. 6 is a diagram illustrating the light-emitting states of the LD in the LD light-emitting circuit of FIG. 5.

Unlike the LD light-emitting circuit 2 which decreases the driving current as the quantity to-be-controlled when a high LD 1 temperature is detected, the LD light-emitting circuit 2A shown here controls the interval between emissions of light as the quantity to-be-controlled. More particularly, when the temperature of the LD 1 is not higher than normal and is functioning properly, the LD 1 emits light, for example, for 1 ms as shown in FIG. 6 in response to the above-mentioned signal of the low potential fed to the terminal CON 1 from the control circuit 7. Thereafter, the light is extinguished for, for example, one second in response to the signal of the high potential. The above operation is repeated again and again hereinafter. However, when the LD 1 heats up to a high temperature such as 60° C. which is not desirable for the LD 1, only the quantity to-be-controlled is changed, i.e., only the interval between light emissions is increased to, for example 1.3 seconds without changing the time for emitting light or the amount of emitted light. When the LD 1 heats up to a high temperature 2, i.e. 80° C., again, only the interval between emissions of light is increased to, for example, 1.5 seconds. Thus, the energy of light emitted within a unit of time is decreased, i.e., power loss is decreased to prevent a rise in temperature of the LD 1 and to lengthen the life of the LD 1.

When an abnormally high temperature for the LD 1, that is, a temperature which is higher than the high temperature 2 (80° C.), is detected, the control circuit 7 feeds the signal of the high potential to both the LD light-emitting circuits 2 and 2A, so that the LD 1 no longer emits light, and sends an alarm to the control unit. The abnormally high temperature of the LD 1 might possibly result from its exposure to hot air currents in addition to its self heating. In such a case, the control unit could make a judgement that there is a possibility a fire has broken out.

Figure 7:
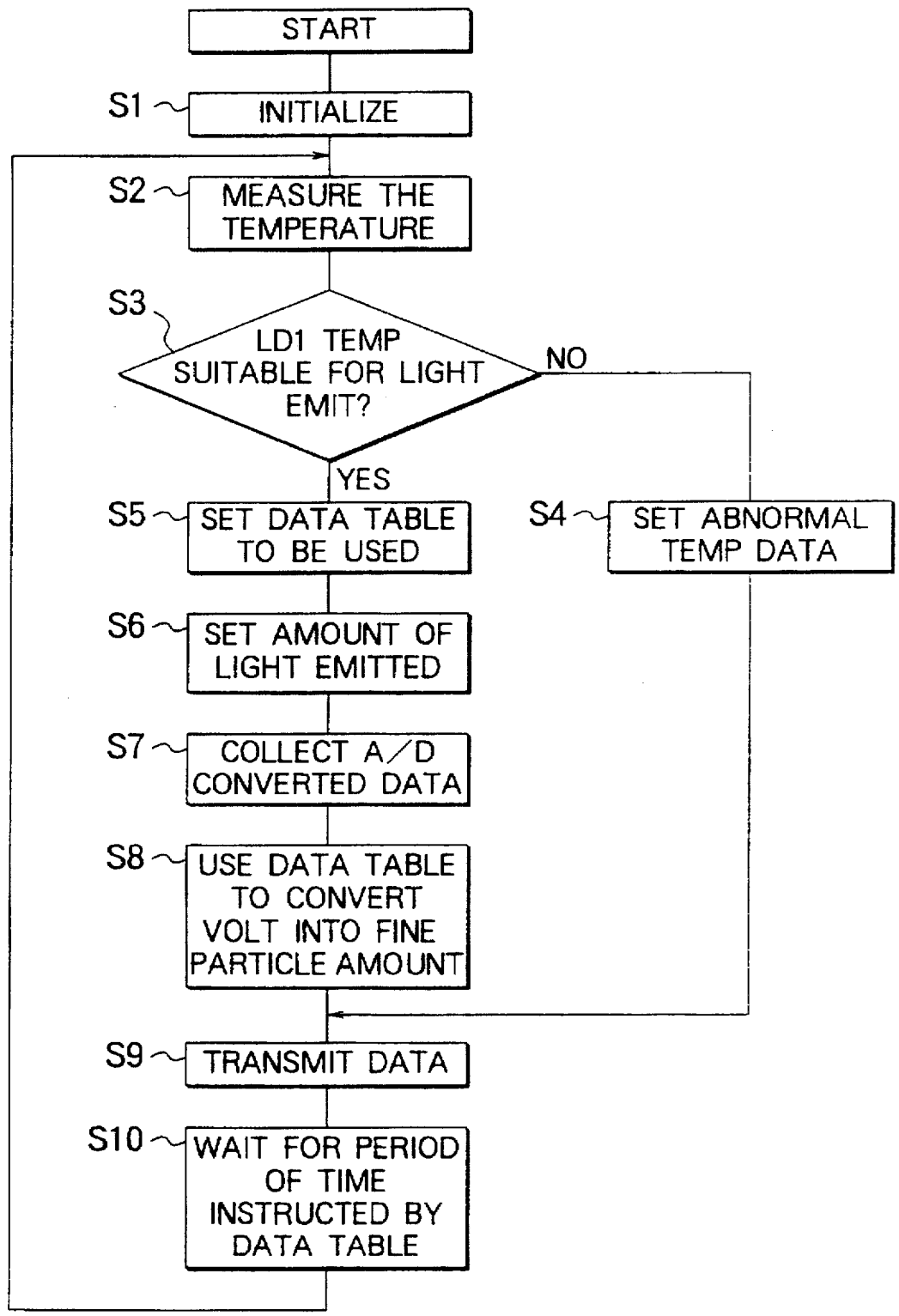
FIG. 7 is a flow chart for explaining the operation of embodiment 1 of the present invention.

FIG. 7 is a flow chart explaining the operation of the sensor for detecting fine particles shown in FIG. 1. In step S1, the ROM and the like are initialized through a predetermined processing of the microprocessor in the control circuit 7. In step S2, the temperature-sensing element 3 measures the temperature of the LD 1 and stores the measured temperature in the RAM 1 in the control circuit 7.

In step S3, it is judged whether the measured temperature read from the RAM 1 is within a temperature range suited for the LD 1 to emit light or not. When the answer is "NO", the program proceeds to step S4 where the abnormal temperature (high temperature) data is written into the RAM 2 in the control circuit 7. The control circuit 7 feeds the signal of the high potential to the LD light-emitting circuit 2 or 2A as described above, so that the LD 1 no longer emits light, and also sends an alarm signal indicating abnormal temperature to the control unit.

Figure 8:
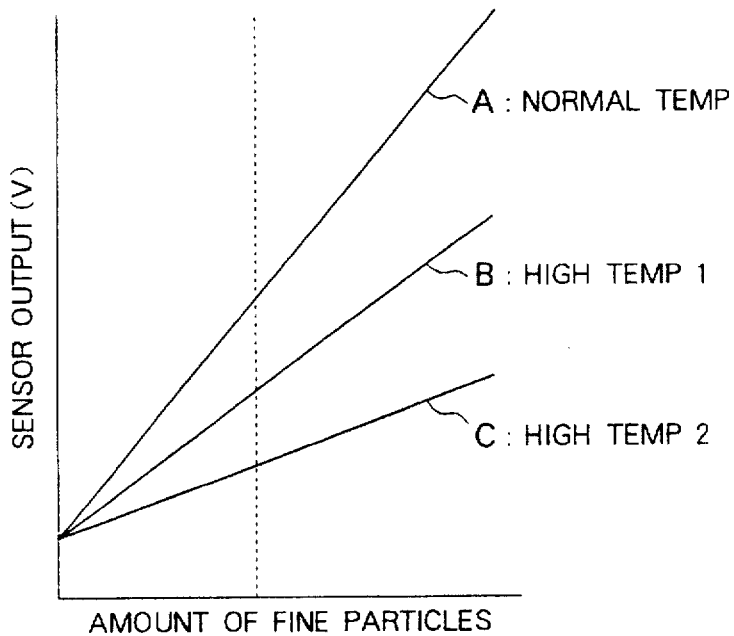
FIG. 8 is a graph showing a conversion data table.

However, when the result of the decision in step S3 is "YES", the program proceeds to step S5. As described above, the amount of light emitted by the LD 1 varies depending upon the temperature. By possessing in the ROM a conversion data table of sensor outputs vs. amount of fine particles (smoke concentration) corresponding to the emitted light, and therefore temperature, the control circuit 7 is able to take a correct measurement. FIG. 8 is a graph illustrating such a data table. FIG. 8 illustrates the state where the sensor output characteristics for the amount of smoke, i.e., for the amount of fine particles, vary depending upon the temperature, such as a normal temperature, high temperature 1 and high temperature 2. By tabulating these relationships in the ROM, it is possible to learn the amount of fine particles to which the sensor output at a given temperature corresponds. Therefore, even if the amount of emitted light changes, smoke can be correctly detected. In step S5, when the temperature being measured is, for example, a normal temperature, the control circuit 7 selects the data table A. Then, the extreme left switch in the analog multiplexer MP in the LD light-emitting circuit 2 shown in FIG. 2 is closed by a signal retrieved from the data table A to connect the resistor R7 to the circuit. Furthermore, at this moment, resistance, constant light-emitting time and interval between emissions of light are written into the RAM 3.

When the temperature measured is as high as, for example, high temperature 1 or high temperature 2, the control circuit 7 selects data table B or C. The switch is then closed by a signal retrieved from data table B or C, and the resistor R8 or R9 is connected.

In the case of the LD light-emitting circuit 2A shown in FIG. 5, the control circuit 7 feeds signals having an interval between emissions of light corresponding to the measured temperature to the LD light-emitting circuit 2A through the terminal CON1, and writes the time interval between emissions of light into the RAM 3.

Then, in step S6, the LD 1 emits the predetermined amount of light as described above.

In step S7, the PD 4 for producing sensor output detects light that is emitted from the LD 1 and scattered by fine particles such as smoke produced by a fire or dust contained in air. Then, the output from the PD is processed by, for example, peak holding or sample holding, as necessary by the PD light-receiving circuit 5 which produces a sensor output. This sensor output is converted into a digital value through the A/D converter circuit 6 and is stored in the RAM 4 in the control circuit 7.

In step S8, the sensor output (voltage) is converted into the amount of fine particles by using the data table selected in step S5, and the result is written into the RAM 2.

In step S9, the control circuit 7 transmits the data written into the RAM 2 in step S4 or S8 to the control unit where the break out of a fire or the detection of fine particles is judged. Finally, in step S10, after having waited a predetermined period of time or the time interval between emissions of light written into the RAM 3 in step S5, the program returns to step S2 to continue detection of fine particles. After time has lapsed and if the temperature has returned a normal temperature, the driving current or the period of non-light emission is returned to the initial state by the control circuit 7. The time for emitting light may be shortened instead of changing the period for emitting light.

Embodiment 2

In embodiment 1, temperature-sensing element 3 is provided, and the driving current as the quantity to-be-controlled for the light source decreases when the temperature increases. In embodiment 2, on the other hand, the driving current for the light source is changed when sensitivity changes.

In the block diagram of FIG. 1 in this case, the control circuit 7 is provided with a means for switching the sensitivity of the fine particle sensor such as a dip switch DP, instead of the temperature-sensing element 3. This switch makes it possible to set the sensitivity in, for example, three to four steps. When the sensitivity is switched, the control circuit 7 feeds to the LD light-emitting circuit 2 a signal for changing the amount of emitted light by changing the driving current fed to the light source so as to meet the new sensitivity. In the analog multiplexer MP shown in FIG. 2, the extreme left switch and the resistor R7 which has the least resistance connected to this switch are for setting high sensitivity.

Figure 9:
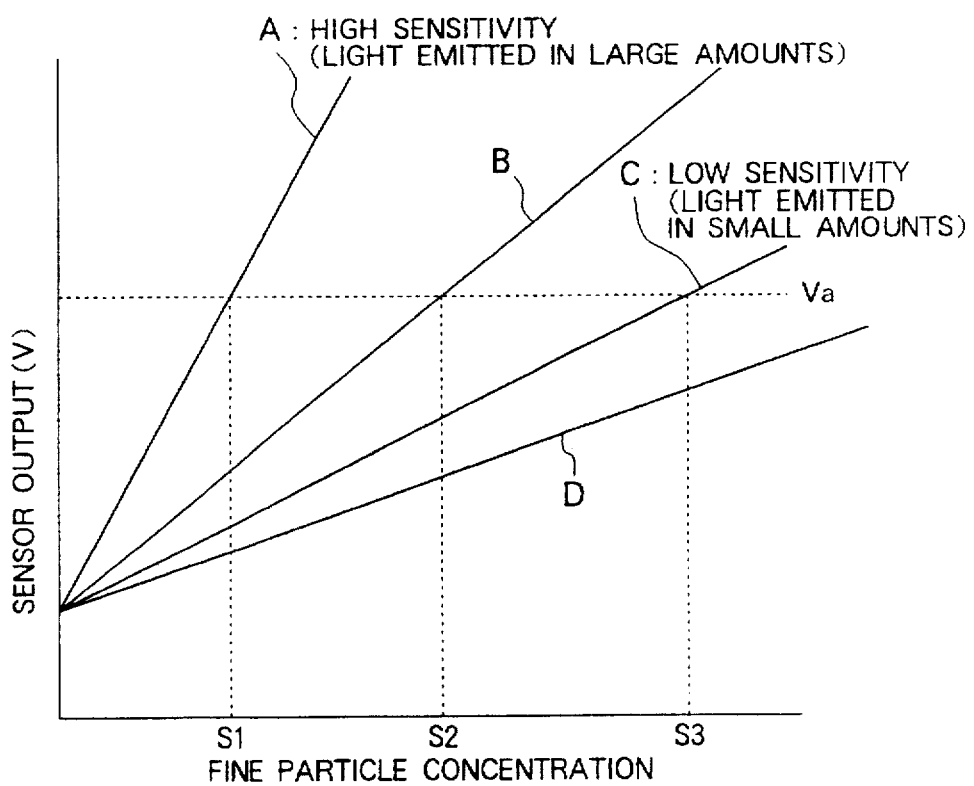
FIG. 9 is a graph showing another conversion data table.

FIG. 9 is a graph showing a data table for converting the sensor output stored in the ROM in the control circuit 7, wherein Va represents an alarm level. FIG. 9 illustrates a state where the sensor output characteristics for the amount of smoke, i.e., for the amount of fine particles, change depending upon the amount of emitted light, i.e., depending upon A, B, C and D. By tabulating these relationships in the ROM, it is possible to know which amount of fine particles the sensor output at any given amount of emitted light corresponds to. It is therefore possible to correctly detect smoke even when the amount of emitted light changes. A data table A represents the state wherein a high sensitivity is set by connecting the resistor R7 of FIG. 2 to the LD light-emitting circuit 2, and the sensor output reaches alarm level Va the moment the concentration of fine particles reaches S1. In a data table B representing the state wherein an intermediate sensitivity is set by connecting the resistor R8, however, sensor output does not reach the alarm level Va until the concentration of fine particles reaches S2. Similarly, in a data table C representing the state wherein a low sensitivity is set by connecting the resistor R9, the sensor output does not reach the alarm level Va until the concentration of fine particles reaches S3. In a data table D representing the state wherein a very low sensitivity is set by connecting the resistor R10, the sensor output does not reach the alarm level Va even after the concentration of fine particles has exceeded S3 by a considerable amount.

In FIG. 9, the data tables A, B, C and D are represented by straight lines rising toward the right. In practice, however, after having arrived at a certain concentration of fine particles (saturation region), the sensor output no longer rises. Therefore, as it remains at a high level of sensitivity, it is no longer possible to correctly measure very high concentrations of fine particles.

As will be obvious from data tables A to D, when the concentration of fine particles remains the same, e.g., remains at S1, the sensor output or the amount of light emitted by the LD 1 may be decreased with a decrease in the sensitivity. According to the present invention, therefore, when the sensitivity is set low by operating the switch for setting sensitivity (e.g., when data table A is changed into data table B), the control circuit 7 outputs a signal to select and close the switch to which the resistor R8 having a resistance larger than the resistor R7 is connected instead of selecting and closing the switch to which the resistor R7 is connected. Then, as in the above-mentioned case (embodiment 1), the driving current flowing into the LD 1 is decreased, i.e., the amount of light emitted by the LD 1 is decreased and, hence, less electric power is consumed by the LD 1 and the life of the LD 1 is increased.

As the sensitivity decreases further (see data tables C and D), the resistor R9 is selected and connected instead of the resistor R8, or the resistor R10 is selected and connected instead of the resistor R9, so that the driving current and the amount of emitted light decrease further.

Figure 10:
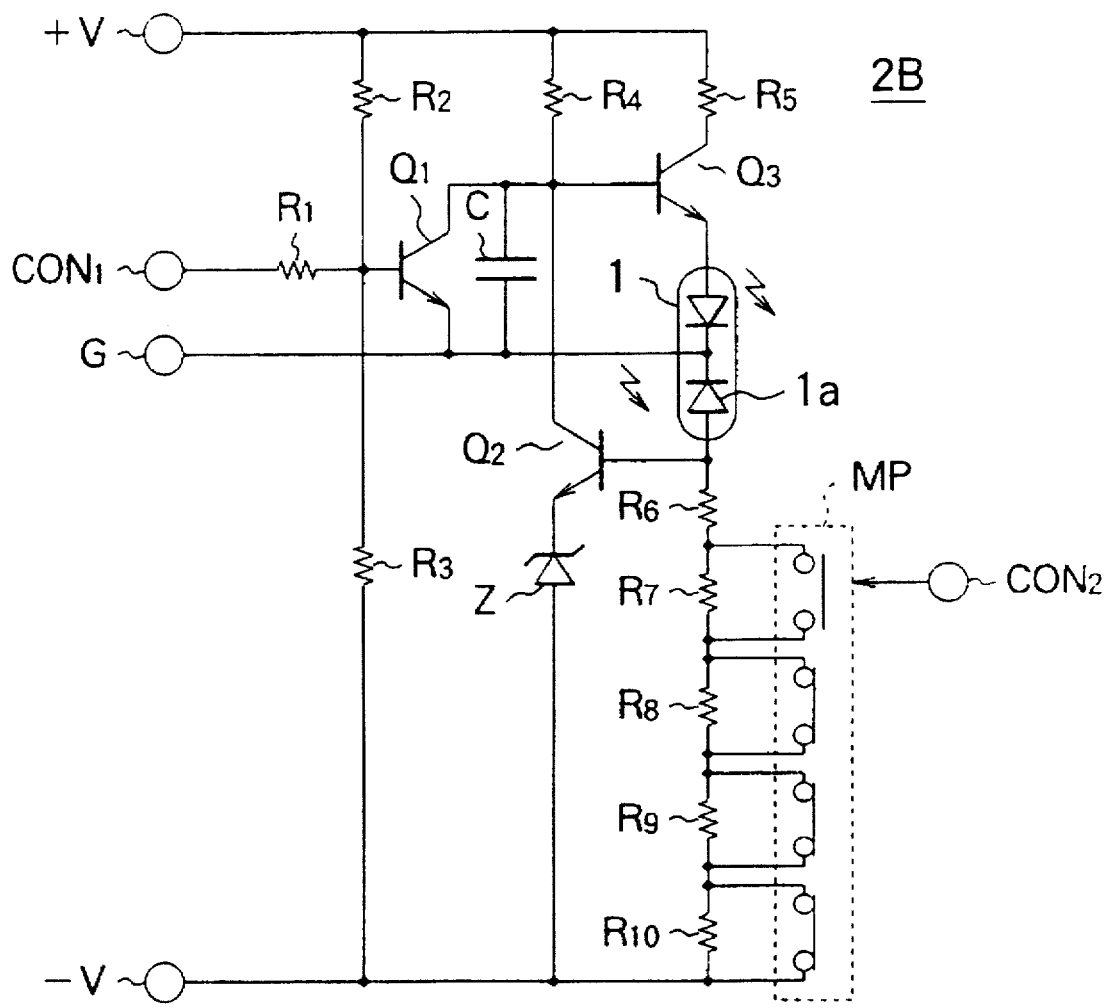
FIG. 10 is a diagram illustrating a further LD light-emitting circuit.

In the LD light-emitting circuit 2 shown in FIG. 2, a corresponding resistor is connected to the circuit by closing a switch using a signal from the control circuit 7. However, the corresponding resistor may be connected to the circuit by opening the switch. FIG. 10 illustrates an example of this case. With this LD light-emitting circuit 2B, the switches connected to the resistors R8 to R10 are opened successively by signals fed through the terminal CON2 as sensitivity decreases. When a low sensitivity is selected, there is no need to particularly close the switch connected to the resistor R7.

In the LD light-emitting circuit 2 of FIG. 2 and in the LD light-emitting circuit 2B of FIG. 10, the amount of emitted light decreases each time the sensitivity is switched to the lower side as described above. In any case, in the high sensitivity data table A, saturation takes place between the fine particle concentration S1 and the fine particle concentration S2. By controlling through the control circuit 7 so the data table is switched to data table B when S1 is exceeded and to the less sensitive data table C or D when S2 or S3 is exceeded, the data table D is saturated only after S3 is exceeded by a considerable amount. Therefore, in the end, the effect of an expanded dynamic range is achieved.

Figure 11:
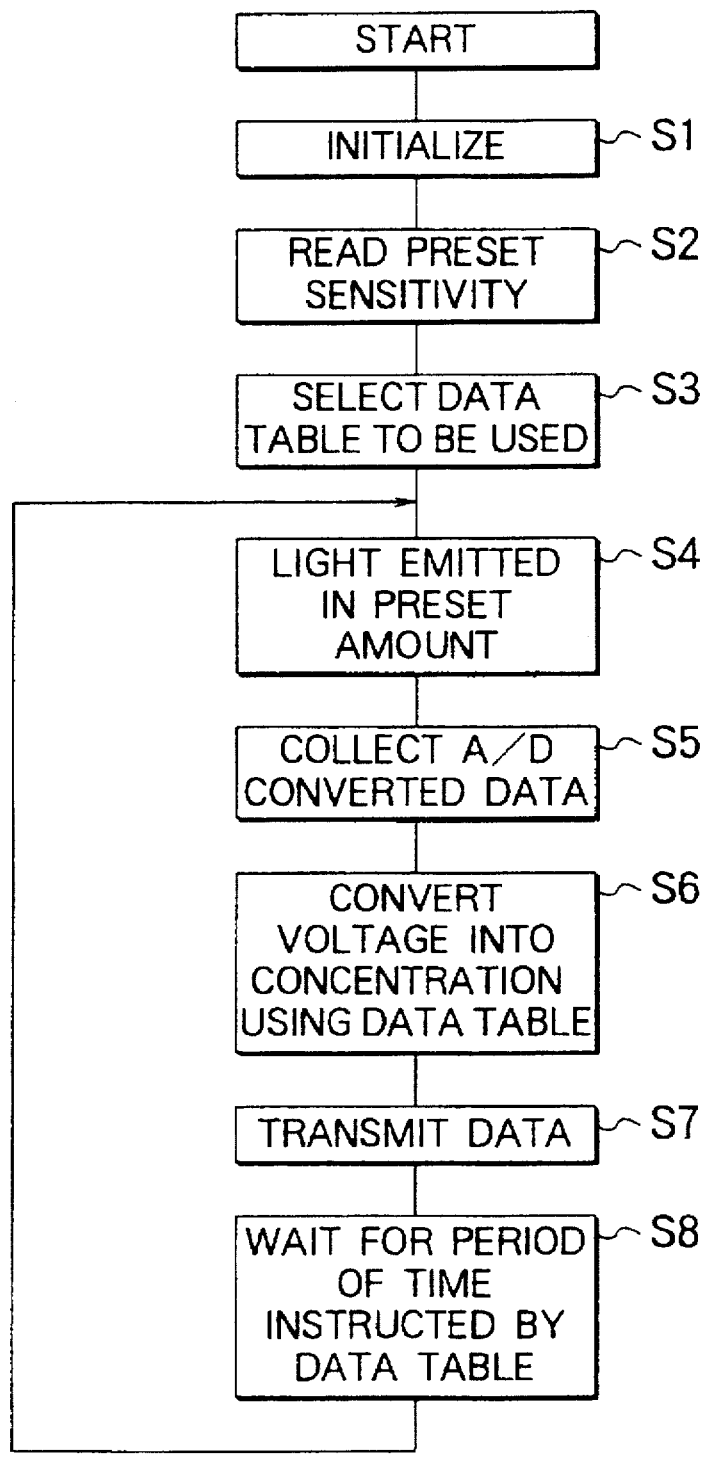
FIG. 11 is a flow chart for explaining the operation of embodiment 2 of the present invention.

FIG. 11 is a flow chart for explaining the operation of the sensor for detecting fine particles shown in FIG. 1. In step S1, the ROM and the like are initialized through a predetermined processing of the microprocessor in the control circuit 7. Next, in step S2, the present alarm level Va, i.e., sensitivity or full-scale measurement, is read and stored in the RAM 1.

In step S3, a data table for converting the sensor output (amount of emitted light) into a concentration of fine particles is selected depending upon the data read out from the RAM 1. When a high sensitivity is set, for instance, data table A is selected so that light is emitted in large amounts from the LD 1. When a low sensitivity is set, data table C is selected so that light is emitted in small amounts, and the preset amount of emitted light is stored in the RAM 2.

In step S4, a predetermined resistor is connected to the terminal CON2 of the LD light-emitting circuit 2 or 2A based upon a value in the RAM 2 in response to a signal fed from the control circuit 7. Then, the LD 1 emits light in a preset amount in response to a signal fed to the CON1.

In step S5, the PD 4 for producing sensor output receives light that is emitted from the LD 1 and scattered by fine particles such as smoke produced by a fire or dust contained in air. Then, this output of the PD is processed by, for example, peak holding or sample holding, as necessary, by the PD light-receiving circuit 5 which produces a sensor output. The sensor output is converted into a digital value through the A/D converter circuit 6 and is stored in the RAM 3.

In step S6, the data in the RAM 3 is subjected to the voltage/concentration conversion based upon a data table selected in step S3, and returned to the RAM 3. In step S7, the control circuit 7 transmits the data from RAM 3 to the control unit. Finally, in step S8, after having waited for a data table value, the program returns to step S4 to continue the detection of fine particles. This wait time may be omitted when it is not necessary. After step S8, it is also possible for the control circuit 7 to judge whether the sensor output has reached a saturation region or not. When the saturation region is reached, sensitivity may be lowered by one step.

Embodiment 2 exemplifies the case wherein sensitivity was first set at a high sensitivity and was incrementally moved toward a low sensitivity. It is, however, also possible to first set a low sensitivity, and then, switch to a high sensitivity.

Moreover, provision of a light-receiving element for monitoring the amount of light emitted from the light source makes it possible to determine whether the sensitivity of the sensor is actually switched when sensitivity is switched. Conventionally, it has not been possible on the sensor side to determine whether sensitivity was actually switched or not.

According to the above-mentioned embodiments, a single LD is used and the driving current is decreased when a low sensitivity is set to decrease the amount of emitted light. It is, however, also possible to use a plurality of light sources and to limit the number of light sources for light emission when a low sensitivity is selected. Rather than constantly sending the sensor output to the control unit, by providing the sensor for detecting fine particles with a discrimination circuit the results of discrimination may be sent only when required. Moreover, the sensor output and the result of discrimination may be sent in response to a polling signal from the control unit. Furthermore, in embodiment 2, a switch for setting sensitivity may be provided on the control unit side, and in addition to an LD, the light source may be an LED, a xenon lamp, etc.

What is claimed is:

1. A sensor for detecting fine particles such as smoke produced by a fire or dust contained in air, comprising:
   a light source;
   a light-emitting circuit electrically connected to the light source for causing light to be emitted from the light source and for keeping the amount of emitted light constant;
   light-receiving means for producing a sensor output upon detecting light scattered by the presence of fine particles in the light emitted from said light source;
   control means electrically connected to said light-emitting means for controlling a driving current of said light source; and
   temperature-measuring means for measuring the temperature of said light source;
   wherein said control means controls the driving current of said light source based upon the values of a temperature measured by said temperature-measuring means.

2. A sensor for detecting fine particles according to claim 1, wherein said light-emitting means includes means for decreasing the driving current when said temperature-measuring means detects a high temperature which is not desirable for said light source; and said driving current-decreasing means is controlled by said control means.

3. A sensor for detecting fine particles according to claim 2, wherein said driving current-decreasing means is electrically connected to said light source, and comprises a multiplexer in which any one of a plurality of switches, connected to a resistor, is selected by a signal from said control means.

4. A sensor for detecting fine particles according to claim 2, wherein said driving current-decreasing means is electrically connected to said light source, and comprises an electron volume device of which the resistance is adjusted in response to a signal from said control means.

5. A sensor for detecting fine particles according to claim 1, wherein, when said temperature-measuring means has detected a temperature which is abnormally high for said light source, said control means produces an alarm, and sends a signal for halting the emission of light from said light source to said light-emitting means.

6. A sensor for detecting fine particles according to claim 1, wherein said light source is a laser diode.

7. A sensor for detecting fine particles such as smoke produced by a fire or dust contained in air, comprising:
   a light source;
   light-emitting means electrically connected to the light source for causing light to be emitted therefrom;
   light-receiving means for producing a sensor output upon detecting light scattered by the presence of fine particles in the light emitted from said light source;
   control means electrically connected to said light-emitting means for controlling a non-light emitting interval of said light source; and
   temperature-measuring means for measuring the temperature of said light source;

wherein said control means includes means for feeding to said light-emitting means a signal which increases said non-light emitting interval when said temperature-measuring means has detected a high temperature which is not desirable for said light source.

8. A sensor for detecting fine particles according claim 7, wherein, when said temperature-measuring means has detected a temperature which is abnormally high for said light source, said control means produces an alarm, and sends a signal for halting the emission of light from said light source to said light-emitting means.

9. A sensor for detecting fine particles according to claim 7, wherein said light source is a laser diode.

10. A sensor for detecting fine particles such as smoke produced by a fire or dust contained in air, comprising:
   a light source;
   light-emitting means electrically connected to the light source for causing light to be emitted therefrom;
   light-receiving means for producing a sensor output upon detecting light scattered by the presence of fine particles in the light emitted from said light source; and
   control means electrically connected to said light-emitting means for controlling a driving current of said light source;
   wherein said control means is provided with sensitivity switching means for switching the sensitivity of the sensor for detecting fine particles, and when the sensitivity of the sensor for detecting fine particles is switched by said sensitivity switching means, said control means feeds to said light-emitting means a signal for changing the amount of emitted light by changing the driving current fed to said light source so as to correspond to the sensitivity.

11. A sensor for detecting fine particles according to claim 10, wherein, when the concentration of fine particles has reached the saturation region of a present sensitivity, said control means controls said sensitivity switching means to switch the sensitivity toward a low sensitivity.

12. A sensor for detecting fine particles according to claim 10, wherein said light-emitting means includes means for decreasing said driving current in response to a signal fed from said control means.

13. A sensor for detecting fine particles according to claim 12, wherein said driving current-decreasing means is electrically connected to said light source, and comprises a multiplexer in which any one of a plurality of switches, connected to a resistor, is selected by a signal from said control means.

14. A sensor for detecting fine particles according to claim 12, wherein said driving current-decreasing means is electrically connected to said light source, and comprises an electron volume device of which the resistance is adjusted in response to a signal from said control means.

15. A sensor for detecting fine particles according claim 10, wherein, when said temperature-measuring means has detected a temperature which is abnormally high for said light source, said control means produces an alarm, and sends a signal for halting the emission of light from said light source to said light-emitting means.

16. A sensor for detecting fine particles according to claim 10, wherein said light source is a laser diode.

* * * * *